US 9,322,800 B2

(12) United States Patent
McColl et al.

(10) Patent No.: US 9,322,800 B2
(45) Date of Patent: Apr. 26, 2016

(54) HEMATOCRIT CORRECTED GLUCOSE MEASUREMENTS USING PHASE ANGLES AND IMPEDANCE FOR ELECTROCHEMICAL TEST STRIP

(75) Inventors: David McColl, Inverness (GB); Mandip Farmahan, Inverness (GB); Antony Smith, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 136 days.

(21) Appl. No.: 13/261,834

(22) PCT Filed: Aug. 31, 2012

(86) PCT No.: PCT/EP2012/067020
§ 371 (c)(1),
(2), (4) Date: Mar. 28, 2014

(87) PCT Pub. No.: WO2013/030369
PCT Pub. Date: Mar. 7, 2013

(65) Prior Publication Data
US 2014/0231273 A1    Aug. 21, 2014

Related U.S. Application Data

(60) Provisional application No. 61/530,808, filed on Sep. 2, 2011.

(51) Int. Cl.
*G01N 27/327* (2006.01)
*G01N 27/416* (2006.01)

(52) U.S. Cl.
CPC .......... *G01N 27/416* (2013.01); *G01N 27/3274* (2013.01)

(58) Field of Classification Search
None
See application file for complete search history.

(56) References Cited

U.S. PATENT DOCUMENTS

| 2003/0064525 | A1 | 4/2003 | Beaty et al. |
| 2003/0196874 | A1 | 10/2003 | Cai et al. |
| 2003/0196894 | A1 | 10/2003 | Cai et al. |
| 2011/0139634 | A1 | 6/2011 | Chou et al. |
| 2011/0168575 | A1 | 7/2011 | Lica et al. |
| 2012/0111739 | A1* | 5/2012 | Pasqua ............... G01N 27/3271 205/777.5 |

FOREIGN PATENT DOCUMENTS

| EP | 1394545 A1 | 3/2004 |
| WO | 2006070200 | 7/2006 |
| WO | 2008040998 | 4/2008 |

OTHER PUBLICATIONS

International Search Report and the Written Opinion of the International Searching Authority, PCT/EP2012/067020; Date of mailing—Nov. 6, 2012.
Patent Examination Report No. 1 issued in related Australian Patent Application No. 2012300836, dated Mar. 7, 2014, 3 pages.
International Preliminary Report on Patentability issued in related International Patent Application No. PCT/EP2012/067020, dated Mar. 4, 2014, 6 pages.

* cited by examiner

*Primary Examiner* — J. Christopher Ball

(57) ABSTRACT

Two techniques of determining hematocrit using impedance and phase angle to determine hematocrit are shown and described for correcting an analyte concentration.

10 Claims, 12 Drawing Sheets

HEMATOCRIT CORRECTED GLUCOSE MEASUREMENTS USING PHASE ANGLES AND IMPEDANCE FOR ELECTROCHEMICAL TEST STRIP

PRIORITY

This application claims the benefits of priority under 35 USC§119, 120, 365 and 371 of prior filed U.S. Provisional Patent Application Ser. No. 61/530,808 filed on Sep. 2, 2011, and International Patent Application PCT/EP2012/067020 filed on Aug. 31, 2012, which applications are incorporated by reference in their entirety hereinto this application as if fully set forth herein.

BACKGROUND

Electrochemical glucose test strips, such as those used in the OneTouch® Ultra® whole blood testing kit, which is available from LifeScan, Inc., are designed to measure the concentration of glucose in a blood sample from patients with diabetes. The measurement of glucose can be based on the selective oxidation of glucose by the enzyme glucose oxidase (GO). The reactions that can occur in a glucose test strip are summarized below in Equations 1 and 2.

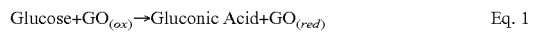

$$\text{Glucose} + GO_{(ox)} \rightarrow \text{Gluconic Acid} + GO_{(red)} \qquad \text{Eq. 1}$$

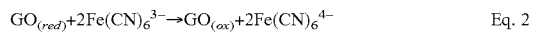

$$GO_{(red)} + 2Fe(CN)_6^{3-} \rightarrow GO_{(ox)} + 2Fe(CN)_6^{4-} \qquad \text{Eq. 2}$$

As illustrated in Equation 1, glucose is oxidized to gluconic acid by the oxidized form of glucose oxidase ($GO_{(ox)}$). It should be noted that $GO_{(ox)}$ may also be referred to as an "oxidized enzyme." During the reaction in Equation 1, the oxidized enzyme $GO_{(ox)}$ is converted to its reduced state, which is denoted as $GO_{(red)}$ (i.e., "reduced enzyme"). Next, the reduced enzyme $GO_{(red)}$ is re-oxidized back to $GO_{(ox)}$ by reaction with $Fe(CN)_6^{3-}$ (referred to as either the oxidized mediator or ferricyanide) as illustrated in Equation 2. During the re-generation of $GO_{(red)}$ back to its oxidized state $GO_{(ox)}$, $Fe(CN)_6^{3-}$ is reduced to $Fe(CN)_6^{4-}$ (referred to as either reduced mediator or ferrocyanide).

When the reactions set forth above are conducted with a test voltage applied between two electrodes, a test current can be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test current generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test current, resulting from the re-oxidation of reduced mediator, and glucose concentration. In particular, the transfer of electrons across the electrical interface results in the flow of a test current (2 moles of electrons for every mole of glucose that is oxidized). The test current resulting from the introduction of glucose can, therefore, be referred to as a glucose current.

Electrochemical biosensors may be adversely affected by the presence of certain blood components that may undesirably affect the measurement and lead to inaccuracies in the detected signal. This inaccuracy may result in an inaccurate glucose reading, leaving the patient unaware of a potentially dangerous blood sugar level, for example. As one example, the blood hematocrit level (i.e. the percentage of the amount of blood that is occupied by red blood cells) can erroneously affect a resulting analyte concentration measurement.

Variations in a volume of red blood cells within blood can cause variations in glucose readings measured with disposable electrochemical test strips. Typically, a negative bias (i.e., lower calculated analyte concentration) is observed at high hematocrit, while a positive bias (i.e., higher calculated analyte concentration) is observed at low hematocrit. At high hematocrit, for example, the red blood cells may impede the reaction of enzymes and electrochemical mediators, reduce the rate of chemistry dissolution since there less plasma volume to solvate the chemical reactants, and slow diffusion of the mediator. These factors can result in a lower than expected glucose reading as less current is produced during the electrochemical process. Conversely, at low hematocrit, fewer red blood cells may affect the electrochemical reaction than expected, and a higher measured current can result. In addition, the blood sample resistance is also hematocrit dependent, which can affect voltage and/or current measurements.

Several strategies have been used to reduce or avoid hematocrit based variations on blood glucose. For example, test strips have been designed to incorporate meshes to remove red blood cells from the samples, or have included various compounds or formulations designed to increase the viscosity of red blood cell and attenuate the affect of low hematocrit on concentration determinations. Other test strips have included lysis agents and systems configured to determine hemoglobin concentration in an attempt to correct hematocrit. Further, biosensors have been configured to measure hematocrit by measuring optical variations after irradiating the blood sample with light, or measuring hematocrit based on a function of sample chamber fill time. These sensors have certain disadvantages.

SUMMARY OF THE DISCLOSURE

Applicants have discovered various embodiments for improved techniques to determine hematocrit in a blood sample in order to arrive at a more accurate analyte concentration. In one aspect, a method to determine analyte concentration in a blood sample is provided. The method can be achieved by: depositing a blood sample in a test chamber of a test strip having at least first and second electrodes in contact with a reagent and third and fourth electrodes not in contact with the reagent; driving a non-oscillating signal to the at least first and second electrodes to cause a reaction with the glucose in the blood sample and the reagent; measuring a current output of the reaction to establish a preliminary analyte concentration; applying a first oscillating input signal at a first frequency to third and fourth electrodes; determining a first estimated hematocrit based on a impedance from output signals of the third and fourth electrodes; applying a second oscillating input signal at a second frequency higher than the first frequency to the third and fourth electrodes; ascertaining a second estimated hematocrit based on a phase angle of output signals from the third and fourth electrodes; estimating a hematocrit of the blood sample based on the first and second estimated hematocrits; and deriving a final analyte concentration based on the preliminary analyte concentration and the hematocrit from the estimating step. In a variation of this method, the second frequency may be one order of magnitude higher than the first frequency; alternatively, the first frequency may be any frequency in a range of about 20,000 Hertz to about 60,000 Hertz and the second frequency comprises any frequency in a range from about 100 kiloHertz to about 1 Mega Hertz. In a further variation, a first frequency may be about 25,000 Hertz and the second frequency may be about 250,000 Hertz; the determining may include utilizing an equation to determine the first estimated hematocrit $HCT_{est1}$:

$$HCT_{est1} = \frac{|Z| - c1}{m1}$$

where $|Z|$ comprises the measured modulus of impedance of the blood sample at the first frequency, and each of c1 and m1 is a coefficient from calibration for a particular strip design. In yet a further variation, the ascertaining may include utilizing an equation to determine the second estimated hematocrit $HCT_{est2}$ of the form:

$$HCT_{est2} = \frac{(\Phi - c2)}{m2}$$

where $\Phi$ comprises a measured phase angle of the blood sample at one or more second frequencies higher than the first frequency; each of c2 and m2 may be a coefficient obtained by calibration depending on a particular strip design. Alternatively, in a variation, the ascertaining may include utilizing an equation to determine the second estimated hematocrit $HCT_{est2}$ of the form:

$$HCT_{est2} = \frac{(\Phi_{f2} - \Phi_{f1} - c3)}{m3}$$

where $\Phi_{f2}$ may be about a measured phase angle of the blood sample at the second frequency; On may be about a measured phase angle of the blood sample at the first frequency lower than the second frequency; each of c3 or m3 may be about a coefficient from calibration depending on strip design. In a further variation, the estimating may be utilizing an equation for a final estimated hematocrit $HCT_{final\_est}$ of the form:

$$HCT_{final\_est} = a * HCT_{est1} + (a-1) * HCT_{est2}$$

where $HCT_{est1}$ may be the first estimated hematocrit, $HCT_{est2}$ may be a second estimated hematocrit and a≤1 to allow for appropriate weighting of the 2 haematocrit measures, such as, for example, 60% for one estimate and 40% for the other estimate.

In this variation, the measuring of a current output for the preliminary analyte concentration is performed prior to the estimating of the hematocrit. In a further variation, the deriving may include calculating the final analyte concentration $G_F$ from:

$$G_F = \frac{\left(\frac{I_E}{1 - k(HCT_{final\_est} - h_0)}\right) - c_4}{m_4}$$

Where $I_E$ comprises a magnitude of the measured end current
$HCT_{final\_est}$ comprises the hematocrit,
$h_0$ comprises nominal hematocrit, and k, $m_4$ and $c_4$ comprise parameters from regressions data.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment. As used herein, "oscillating signal" includes voltage signal(s) or current signal(s) that, respectively, change polarity or alternate direction of current or are multi-directional.

Figure 1:
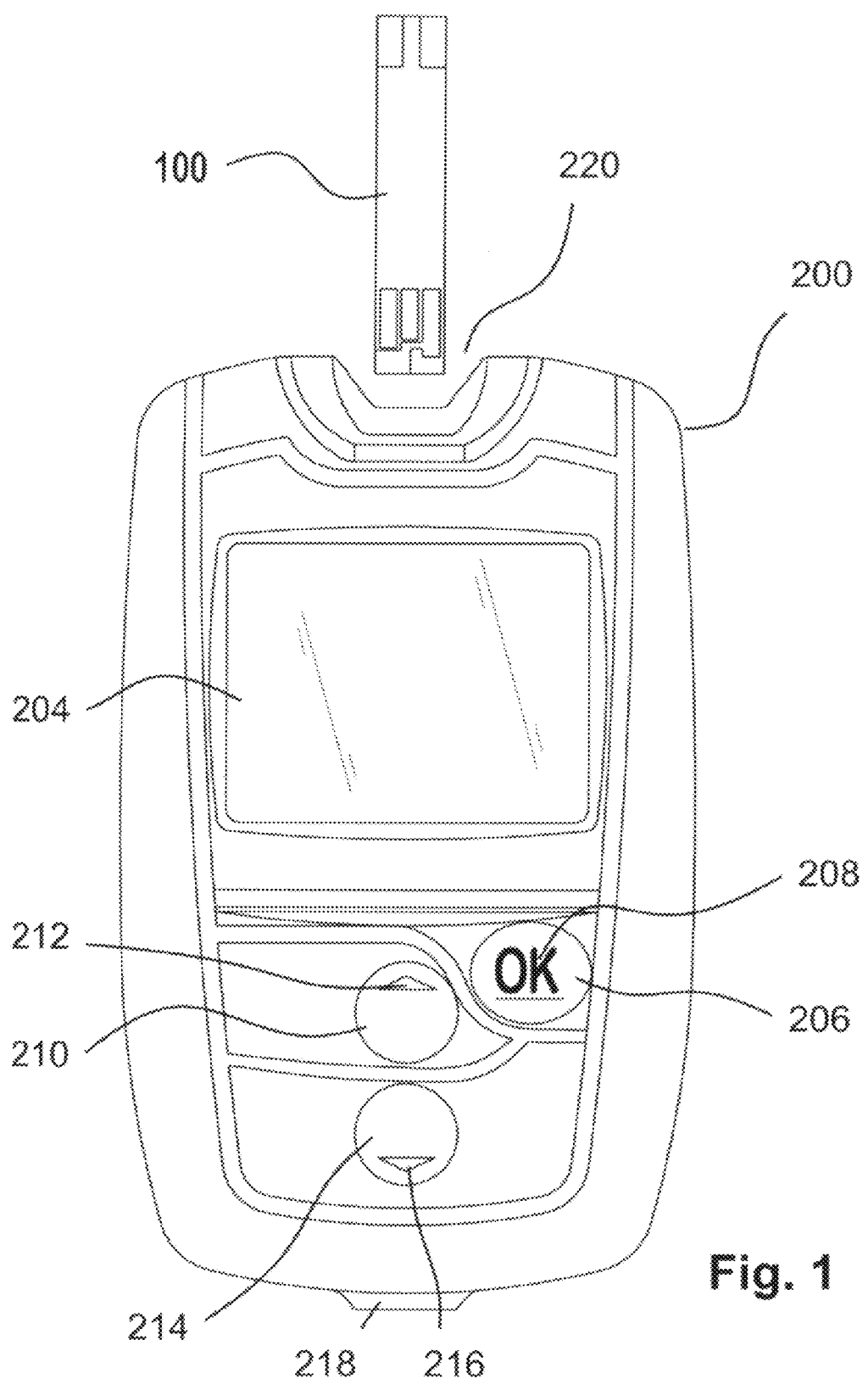
FIG. 1 illustrates an analyte measurement system.

FIG. 1 illustrates a test meter 200, for testing analyte (e.g., glucose) levels in the blood of an individual with a test strip produced by the methods and techniques illustrated and described herein. Test meter 200 may include user interface inputs (206, 210, 214), which can be in the form of buttons, for entry of data, navigation of menus, and execution of commands. Data can include values representative of analyte concentration, and/or information that are related to the everyday lifestyle of an individual. Information, which is related to the everyday lifestyle, can include food intake, medication use, the occurrence of health check-ups, general health condition and exercise levels of an individual. Test meter 200 can also include a display 204 that can be used to report measured glucose levels, and to facilitate entry of lifestyle related information.

Test meter 200 may include a first user interface input 206, a second user interface input 210, and a third user interface input 214. User interface inputs 206, 210, and 214 facilitate entry and analysis of data stored in the testing device, enabling a user to navigate through the user interface displayed on display 204. User interface inputs 206, 210, and 214 include a first marking 208, a second marking 212, and a third marking 216, which help in correlating user interface inputs to characters on display 204.

Test meter 200 can be turned on by inserting a test strip 100 into a strip port connector 220, by pressing and briefly holding first user interface input 206, or by the detection of data traffic across a data port 218. Test meter 200 can be switched off by removing test strip 100, pressing and briefly holding first user interface input 206, navigating to and selecting a meter off option from a main menu screen, or by not pressing any buttons for a predetermined time. Display 104 can optionally include a backlight.

In one embodiment, test meter 200 can be configured to not receive a calibration input for example, from any external source, when switching from a first test strip batch to a second test strip batch. Thus, in one exemplary embodiment, the meter is configured to not receive a calibration input from external sources, such as a user interface (such as inputs 206, 210, 214), an inserted test strip, a separate code key or a code strip, data port 218. Such a calibration input is not necessary when all of the test strip batches have a substantially uniform calibration characteristic. The calibration input can be a set of values ascribed to a particular test strip batch. For example, the calibration input can include a batch slope and a batch intercept value for a particular test strip batch. The calibrations input, such as batch slope and intercept values, may be preset within the meter as will be described below.

Figure 2:
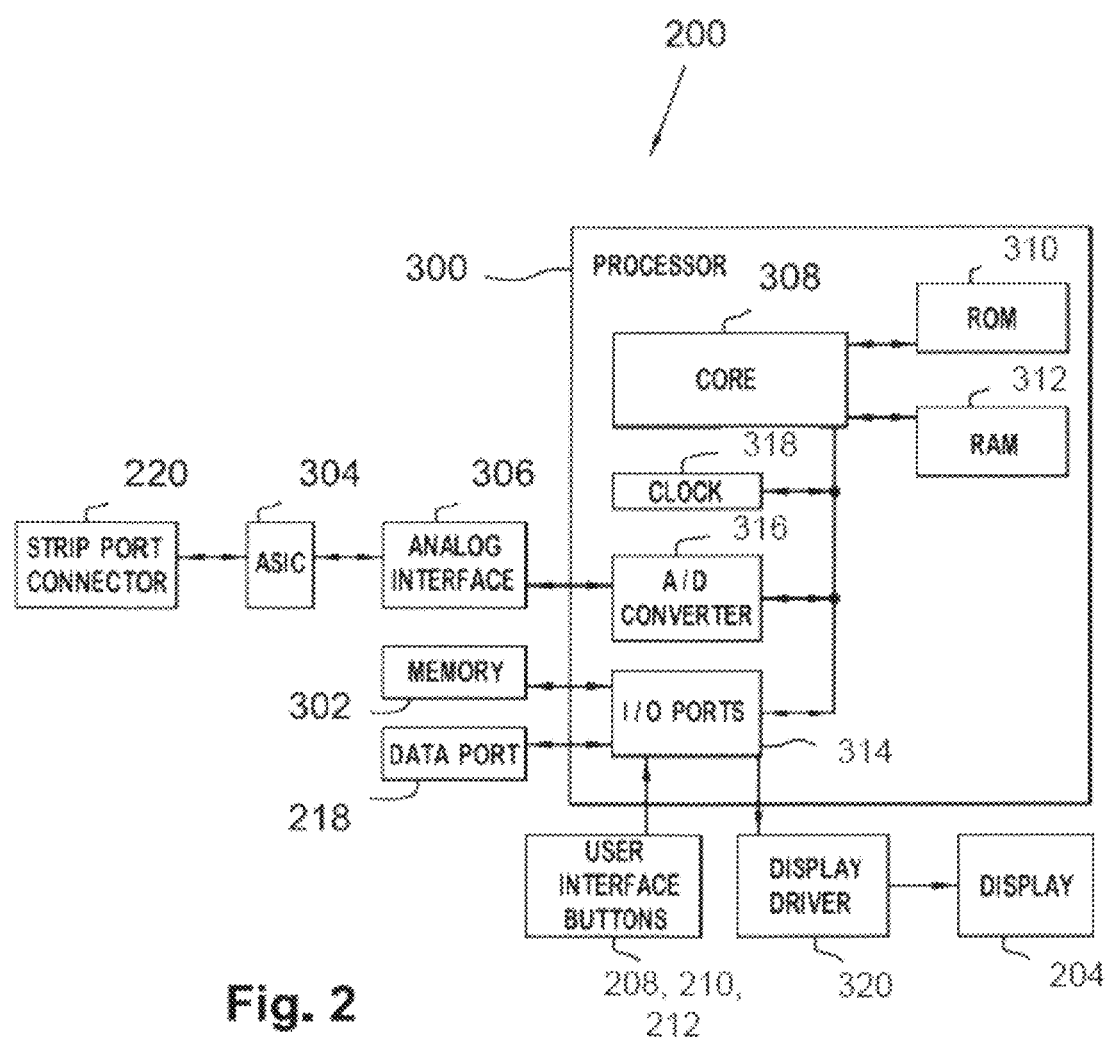
FIG. 2 illustrates in simplified schematic form the components of the meter 200.

Referring to FIG. 2, an exemplary internal layout of test meter 200 is shown. Test meter 200 may include a processor 300, which in some embodiments described and illustrated herein is a 32-bit RISC microcontroller. In the preferred embodiments described and illustrated herein, processor 300 is preferably selected from the MSP 430 family of ultra-low power microcontrollers manufactured by Texas Instruments of Dallas, Tex. The processor can be bi-directionally connected via I/O ports 314 to a memory 302, which in some embodiments described and illustrated herein is an EEPROM. Also connected to processor 300 via I/O ports 214 are the data port 218, the user interface inputs 206, 210, and 214, and a display driver 320. Data port 218 can be connected to processor 300, thereby enabling transfer of data between memory 302 and an external device, such as a personal computer. User interface inputs 206, 210, and 214 are directly connected to processor 300. Processor 300 controls display 204 via display driver 320. Memory 302 may be pre-loaded with calibration information, such as batch slope and batch intercept values, during production of test meter 200. This pre-loaded calibration information can be accessed and used by processor 300 upon receiving a suitable signal (such as current) from the strip via strip port connector 220 so as to calculate a corresponding analyte level (such as blood glucose concentration) using the signal and the calibration information without receiving calibration input from any external source.

In embodiments described and illustrated herein, test meter 200 may include an Application Specific Integrated Circuit (ASIC) 304, so as to provide electronic circuitry used in measurements of glucose level in blood that has been applied to a test strip 100 inserted into strip port connector 220. Analog voltages can pass to and from ASIC 304 by way of an analog interface 306. Analog signals from analog interface 306 can be converted to digital signals by an A/D converter 316. Processor 300 further includes a core 308, a ROM 310 (containing computer code), a RAM 312, and a clock 318. In one embodiment, the processor 300 is configured (or programmed) to disable all of the user interface inputs except for a single input upon a display of an analyte value by the display unit such as, for example, during a time period after an analyte measurement. In an alternative embodiment, the processor 300 is configured (or programmed) to ignore any input from all of the user interface inputs except for a single input upon a display of an analyte value by the display unit. Detailed descriptions and illustrations of the meter 200 are shown and described in International Patent Application Publication No. WO2006070200, which is hereby incorporated by reference into this application as if fully set forth herein, with a copy attached hereto the appendix.

Figure 3A:
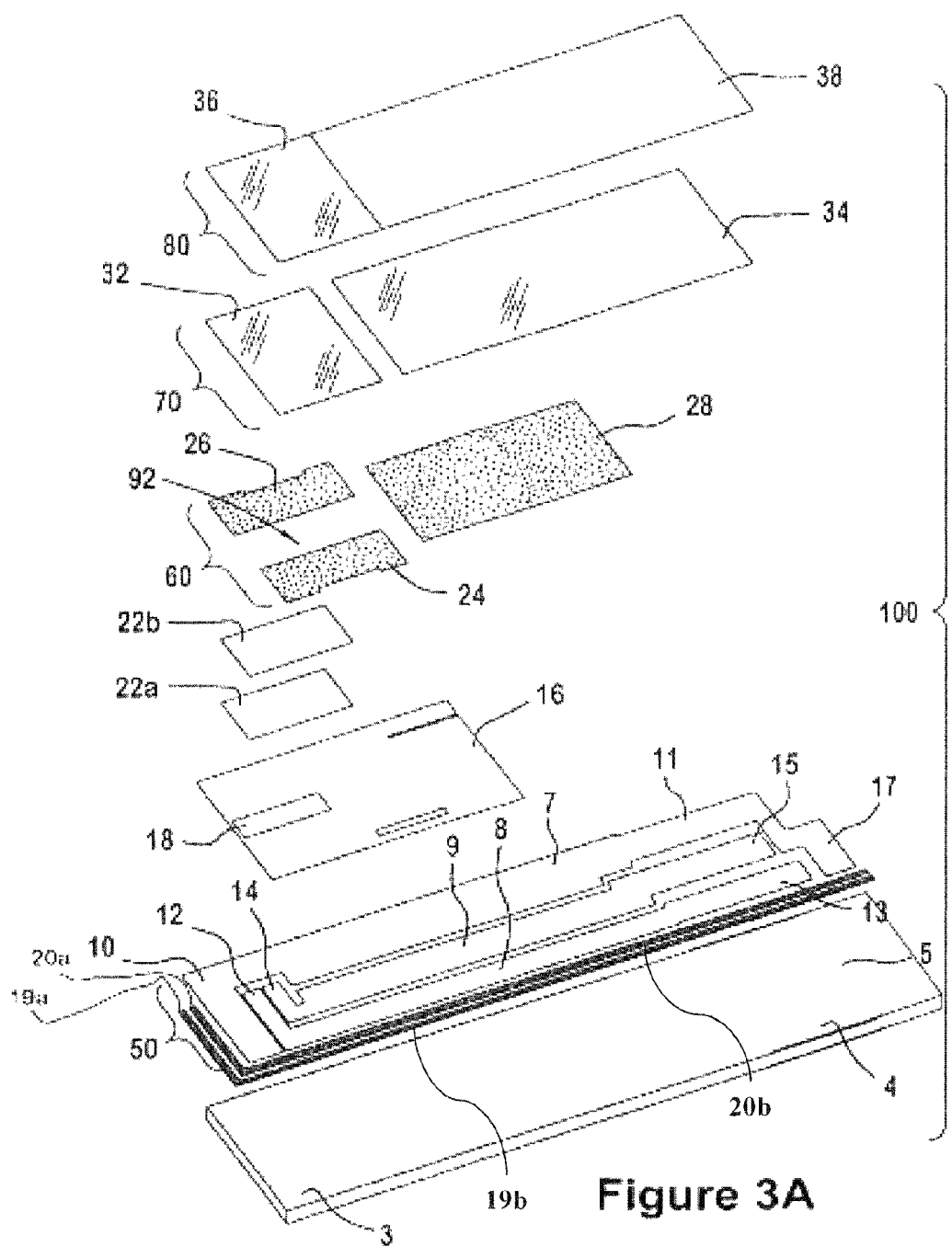
FIG. 3A illustrates the test strip 100 of the system of FIG. 1 in which there are two correction electrodes upstream of the measurement electrodes.

FIG. 3A is an exemplary exploded perspective view of a test strip 100, which may include seven layers disposed on a substrate 5. The seven layers disposed on substrate 5 can be a first conductive layer 50 (which can also be referred to as electrode layer 50), an insulation layer 16, two overlapping reagent layers 22a and 22b, an adhesive layer 60 which includes adhesive portions 24, 26, and 28, a hydrophilic layer 70, and a top layer 80. Test strip 100 may be manufactured in a series of steps where the conductive layer 50, insulation layer 16, reagent layers 22, and adhesive layer 60 are sequentially deposited on substrate 5 using, for example, a screen-printing process. Note that the electrodes 10, 12, and 14) are disposed for contact with the reagent layer 22a and 22b whereas the correction electrodes 19a and 20a are spaced apart and not in contact with the reagent layer 22. Hydrophilic layer 70 and top layer 80 can be disposed from a roll stock and laminated onto substrate 5 as either an integrated laminate or as separate layers. Test strip 100 has a distal portion 3 and a proximal portion 4 as shown in FIG. 3A.

Test strip 100 may include a sample-receiving chamber 92 through which a blood sample may be drawn. Sample-receiving chamber 92 can include an inlet at a proximal end and an outlet at the side edges of test strip 100, as illustrated in FIG. 3A. A blood sample can be applied to the inlet to fill a sample-receiving chamber 92 so that glucose can be measured. The side edges of a first adhesive pad 24 and a second adhesive pad 26 located adjacent to reagent layer 22 each define a wall of sample-receiving chamber 92, as illustrated in FIG. 3A. A bottom portion or "floor" of sample-receiving chamber 92 may include a portion of substrate 5, conductive layer 50, and insulation layer 16, as illustrated in FIG. 3A. A top portion or "roof" of sample-receiving chamber 92 may include distal hydrophilic portion 32, as illustrated in FIG. 3A. For test strip 100, as illustrated in FIG. 3A, substrate 5 can be used as a foundation for helping support subsequently applied layers. Substrate 5 can be in the form of a polyester sheet such as a polyethylene tetraphthalate (PET) material (Hostaphan PET supplied by Mitsubishi). Substrate 5 can be in a roll format, nominally 350 microns thick by 370 millimeters wide and approximately 60 meters in length.

A conductive layer is required for forming electrodes that can be used for the electrochemical measurement of glucose. First conductive layer 50 can be made from a carbon ink that is screen-printed onto substrate 5, gold, silver, silver/silver chloride or palladium. In a screen-printing process, carbon ink is loaded onto a screen and then transferred through the screen using a squeegee. The printed carbon ink can be dried using hot air at about 140° C. The carbon ink can include VAGH resin, carbon black, graphite (KS15), and one or more solvents for the resin, carbon and graphite mixture. More particularly, the carbon ink may incorporate a ratio of carbon black:VAGH resin of about 2.90:1 and a ratio of graphite:carbon black of about 2.62:1 in the carbon ink. Other suitable conductive materials can also be used to form a conductive layer, such as, for example, gold, palladium, platinum, copper, steel, or even conductive polymers.

For test strip 100, as illustrated in FIG. 3A, first conductive layer 50 may include a reference electrode 10, a first working electrode 12, a second working electrode 14, third and fourth correction electrodes 19a and 20a, a first contact pad 13, a second contact pad 15, a reference contact pad 11, a first working electrode track 8, a second working electrode track 9, a reference electrode track 7, and a strip detection bar 17. The correction electrodes 19a and 20a are provided with respective electrode tracks 19b and 20b. The conductive layer may be formed from carbon ink. First contact pad 13, second contact pad 15, and reference contact pad 11 may be adapted to electrically connect to a test meter. First working electrode track 8 provides an electrically continuous pathway from first working electrode 12 to first contact pad 13. Similarly, second working electrode track 9 provides an electrically continuous pathway from second working electrode 14 to second contact pad 15. Similarly, reference electrode track 7 provides an electrically continuous pathway from reference electrode 10 to reference contact pad 11. Strip detection bar 17 is electrically connected to reference contact pad 11. Third and fourth electrode tracks 19b and 20b connect to the respective electrodes 10a and 20a. A test meter can detect that test strip 100 has been properly inserted by measuring a continuity between reference contact pad 11 and strip detection bar 17, as illustrated in FIG. 3A.

Figures 3B, 3C:
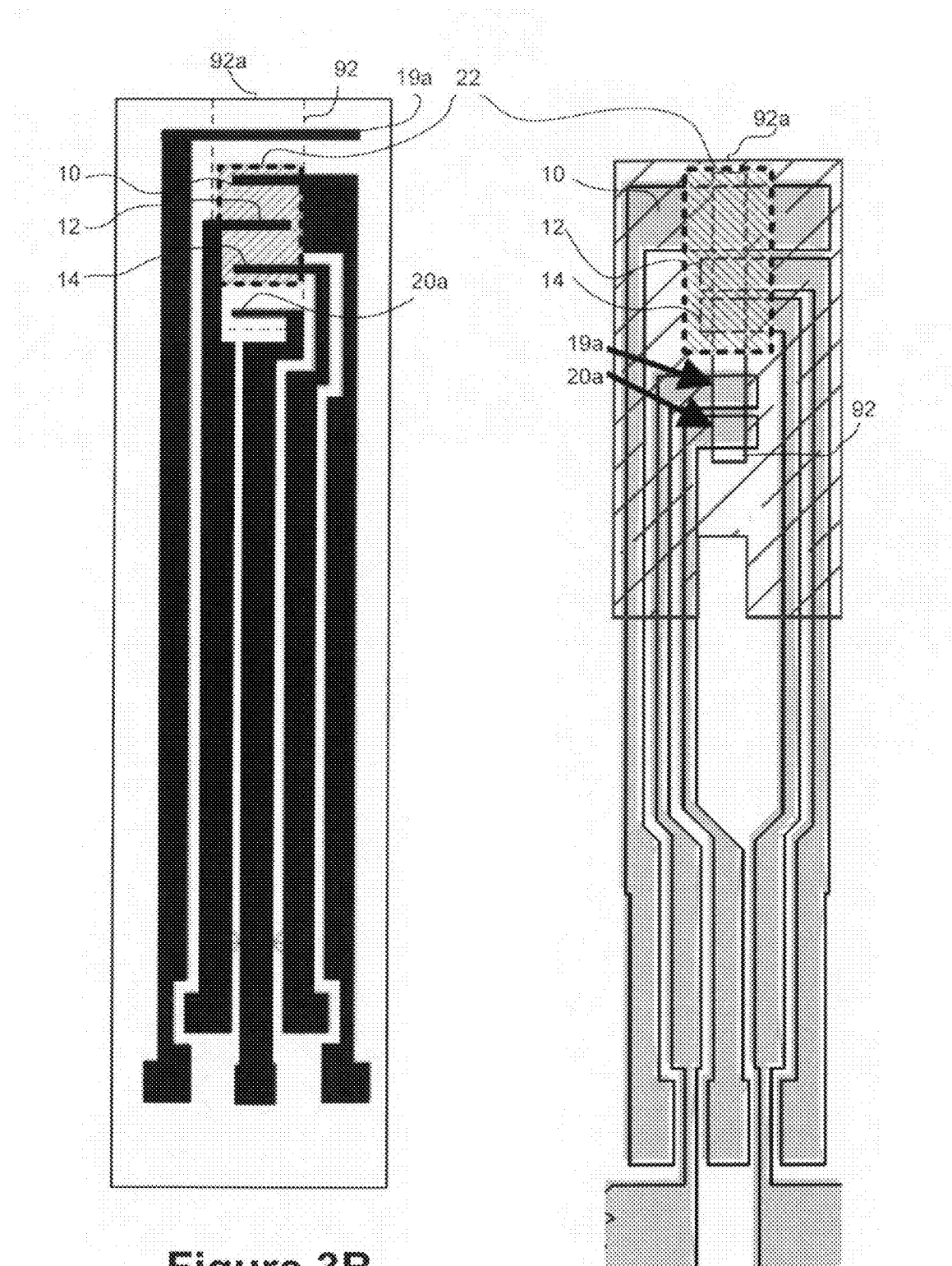
FIG. 3B illustrates a variation of the test strip of FIG. 3A in which one measurement electrode is disposed proximate the entrance and the other measurement electrode is at the terminal end of the test cell with the measurement electrodes disposed between the pair of correction electrodes.
FIGS. 3C and 3D illustrate variations of FIG. 3A in which the correction electrodes are disposed next to each other at the terminal end of the test chamber with the measurement electrodes upstream of the correction electrodes.
Figures 3D, 3E:
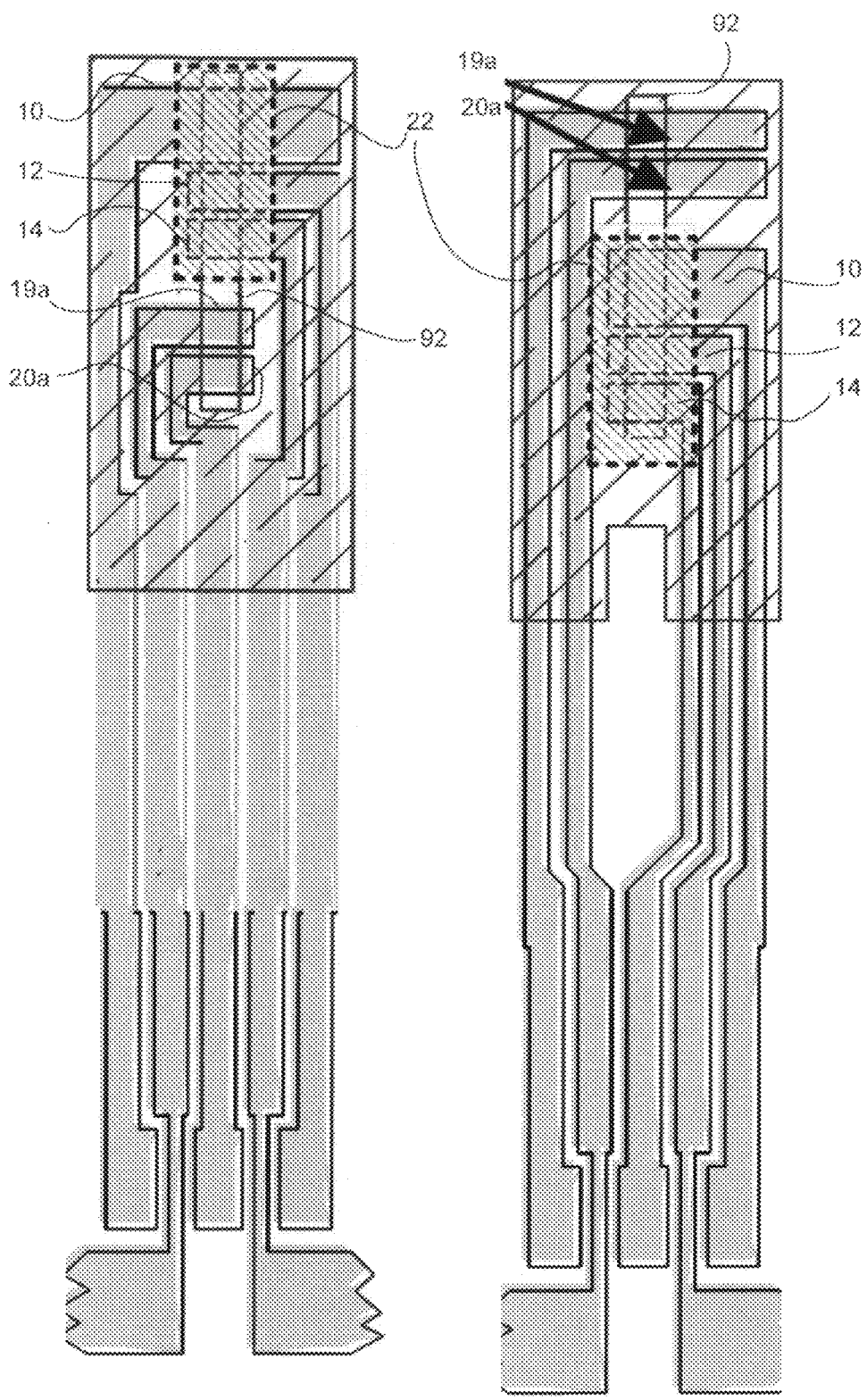
FIGS. 3E and 3F illustrates a correction electrodes arrangement similar to that of FIG. 3A in which the pair of correction electrodes are proximate the entrance of the test chamber.
Figure 3F:
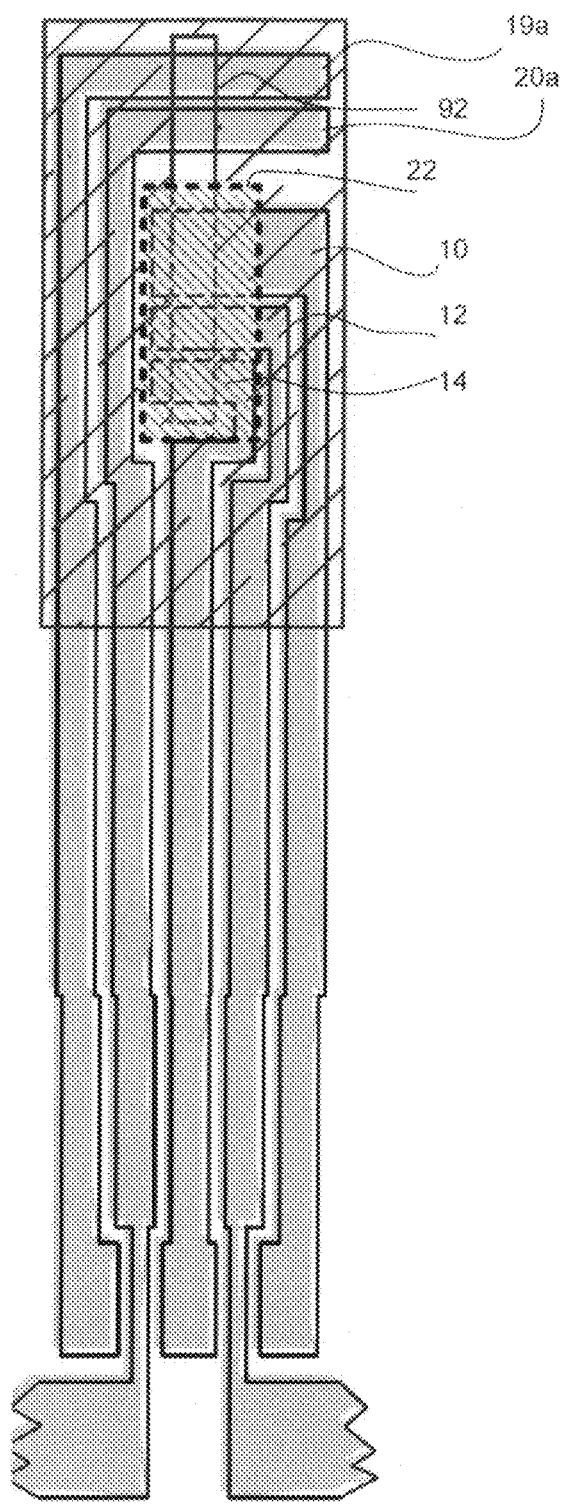

Variations of the test strip 100 (FIG. 3A) are shown in FIGS. 3B, 3C, 3D, 3E, and 3F. In the embodiment of FIG. 3B, the analyte measurement electrodes 10, 12, and 14 are disposed in generally the same configuration as in FIG. 3A. The electrodes 19a and 20a to sense hematocrit level, however, are disposed in a spaced apart configuration in which one electrode 19a is proximate an entrance 92a to the test chamber 92 and another electrode 20a is at the opposite end of the test chamber 92. Electrodes 10, 12, and 14 are disposed to be in contact with a reagent layer 22. In FIGS. 3C, 3D, and 3E, the hematocrit sensing electrodes 19a and 20a are disposed adjacent each other and may be placed at the opposite end 92b of the entrance 92a to the test chamber 92 (FIGS. 3C and 3D) or adjacent the entrance 92a (FIGS. 3E and 3F).

In the various embodiments of the test strip shown and described herein, there are two measurements that are made to a blood sample deposited on the test strip. One measurement is that of the magnitude of glucose in the blood sample (given as milligrams per deciliter) while the other is the magnitude of hematocrit (expressed as a percentage of the blood volume). The measurement of the hematocrit is used to modify or correct the glucose measurement so as to remove or reduce the effect of red blood cells on the glucose measurements. Both measurements (glucose and hematocrit) can be performed in sequence, simultaneously or overlapping in duration. For example, the glucose measurement can be performed first then the hematocrit; the hematocrit measurement first then the glucose measurement; both measurements at the same time; or a duration of one measurement may overlap a duration of the other measurement. Each measurement is discussed in detail as follow with respect to FIGS. 4 and 5.

Figure 4A:
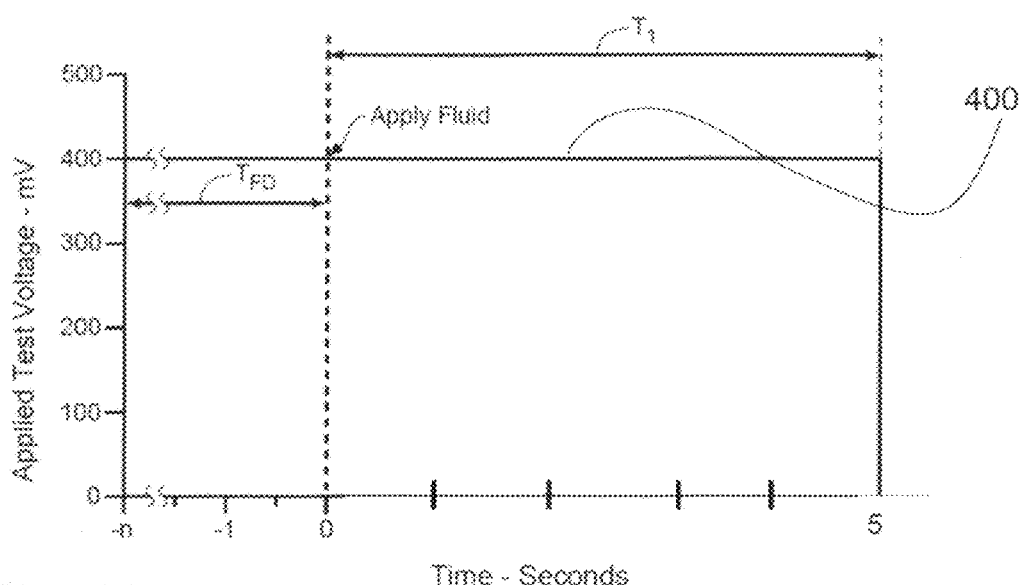
FIG. 4A illustrates a graph of time over applied potential to the test strip of FIG. 1.

FIG. 4A is an exemplary chart of a test voltage applied to test strip 100 and its variations shown here in FIGS. 3A-3F. Before a fluid sample is applied to test strip 100, test meter 200 is in a fluid detection mode in which a first test voltage of about 400 millivolts is applied between second working electrode 14 and reference electrode 10. A second test voltage of about 400 millivolts is preferably applied simultaneously between first working electrode 12 and reference electrode 10. Alternatively, the second test voltage may also be applied contemporaneously such that a time interval of the application of the first test voltage overlaps with a time interval in the application of the second test voltage. The test meter may be in a fluid detection mode during fluid detection time interval $t_{FD}$ prior to the detection of physiological fluid at starting time at zero. In the fluid detection mode, test meter 200 determines when a fluid is applied to test strip 100 such that the fluid wets second working electrode 14 and reference electrode 10. Once test meter 200 recognizes that the physiological fluid has been applied because of, for example, a sufficient increase in the measured test current at second working electrode 14, test meter 200 assigns a zero second marker at zero time "0" and starts the test time interval $T_1$. Upon the completion of the test time interval $T_1$, the test voltage is removed. For simplicity, FIG. 4A only shows the first test voltage applied to test strip 100.

Hereafter, a description of how analyte concentration is determined from the known current transients (i.e., the measured electrical current response in nanoamperes as a function of time) that are measured when the test voltages of FIG. 4A are applied to the known test strip 100.

In FIG. 4A, the first and second test voltages applied to test strip 100 are generally from about +100 millivolts to about +600 millivolts. In one embodiment in which the electrodes include carbon ink and the mediator is ferricyanide, the test voltage is about +400 millivolts. Other mediator and electrode material combinations will require different test voltages. The duration of the test voltages is generally from about 2 to about 4 seconds after a reaction period and is typically about 3 seconds after a reaction period. Typically, time $T_1$ is measured relative to time $t_0$. As the voltage 400 is maintained in FIG. 4A for the duration of T1, the current transient 402 for the first working electrode is generated starting at zero time and likewise the current transient 404 for the second working electrode is also generated with respect to the zero time. The current transients build up to a peak proximate peak time Tp at which time, the current slowly drops off until approximately 5 seconds after zero time. At the point 406, the current value for each of the working electrodes are measured and added together. From knowledge of the calibration code offset and slope for the particular test strip 100, the analyte concentration can be calculated. "Intercept" and "Slope" are the values obtained by measuring calibration data from a batch of test strips. Typically around 1500 strips are selected at random from the lot or batch. Body fluid from donors is spiked to various analyte levels, typically six different analyte concentrations. Typically, blood from 12 different donors is spiked to each of the six levels. Eight strips are given blood from identical donors and levels so that a total of 12×6×8=576 tests are conducted for that lot. These are benchmarked against actual analyte level (e.g., blood glucose concentration) by measuring these using a standard laboratory analyzer such as Yellow Springs Instrument (YSI). A graph of measured analyte concentration is plotted against actual analyte concentration (or measured current versus YSI current), A graph of measured analyte concentration is plotted against actual analyte concentration (or measured current versus YSI current), and a formula y=mx+c least squares fitted to the graph to give a value for batch slope m and batch intercept c for the remaining strips from the lot or batch. In the preferred embodiments, the analyte may include glucose.

Figure 4B:
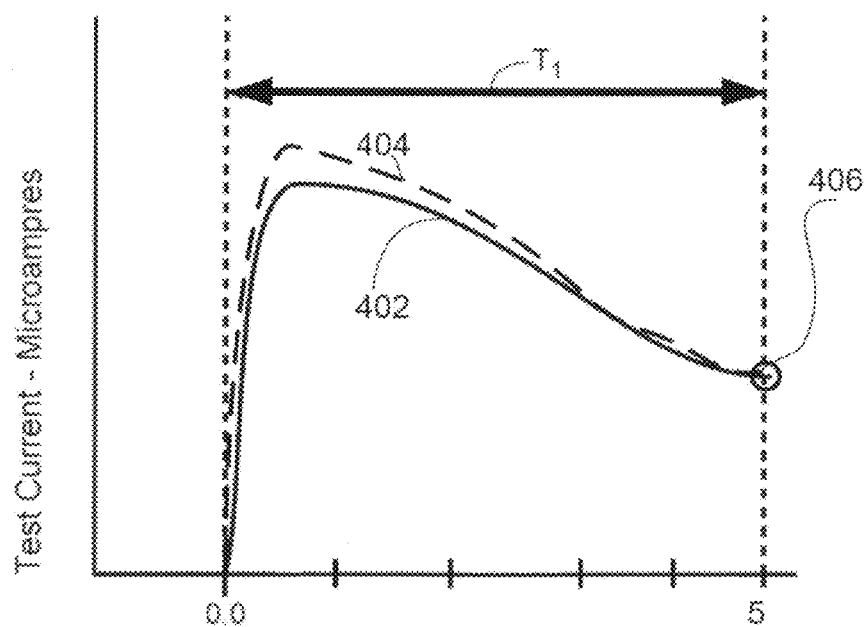
FIG. 4B illustrates a graph of time over output current from the test strip of FIG. 1.

As an example of an analyte calculation (e.g., glucose) for strip 100 (FIG. 3A), it is assumed in FIG. 4B that the sampled current value at 406 for the first working electrode is 1600 nanoamps whereas the current value at 406 for the second working electrode is 1300 nanoamps and for the calibration code of the test strip the Intercept is 500 nanoamps and the Slope is 18 nanoamp/mg/dL. Analyte concentration G can be thereafter be determined from Equation 3 as follow:

$$G = [(I_E) - \text{Intercept}]/\text{Slope} \quad \text{Eq. 3}$$

where
$I_E$ is a preliminary analyte concentration determined from the sum of the end currents measured at both electrodes or $I_{we1} + I_{we2}$
$I_{we1}$ is the current measured for the first working electrode at the end of T1;
$I_{we2}$ is the current measured for the second working electrode at the end of T1;
Slope is the value obtained from calibration testing of a batch of test strip of which this particular strip comes from;
Intercept is the value obtained from calibration testing of a batch of test strip of which this particular strip comes from.

From Eq. 3 G=[(1600+1300)−500]/18 and therefore, G=133.33 nanoamp~133 mg/dL. It is noted that the analyte concentration here is not corrected for any hematocrit value and that certain offsets may be provided to the current value $I_{we1}$ and $I_{we2}$ to account for errors or delay time in the electrical circuit of the meter 200. Temperature compensation can also be utilized to ensure that the results are calibrated to a referential temperature such as for example room temperature of about 20 degrees Celsius.

Now that a preliminary analyte concentration ($I_E$) can be determined from the end currents, a description of applicant's technique to determine the hematocrit of the blood sample is provided in relation to FIGS. 5A-5E. In FIG. 5, the system 200 (FIG. 2) applies a first oscillating input signal at a first frequency (of about 25,0000 Hertz) to a pair of electrodes such as, for example, the third and fourth electrodes 19a and 20a. The system is also set up to measure or detect a first oscillating output signal from the third and fourth electrodes. At the same time or during overlapping time durations, the system may also apply a second oscillating input signal at a second frequency (of about 250,000 Hertz) to a pair of electrodes (e.g., the third and fourth electrodes) and then measure or detect a second oscillating output signal from the third and fourth electrodes. From these signals, the system derives two estimates for hematocrit of the blood sample from the two different signals. The two estimates are combined together to arrive at a final hematocrit estimate. Finally, the system is able to derive a final analyte concentration based on the preliminary analyte concentration and final hematocrit estimate. The technique to derive the two hematocrit estimates are derived as described below:

For this technique, two independent measurements of hematocrit can be obtained by determining: (a) the impedance of the blood sample at a first frequency and (b) the phase angle of the blood sample at a second frequency substantially higher than the first frequency. In this technique, the blood sample is modeled as a circuit having unknown reactance and unknown resistance. With this model, a impedance (as signified by notation "|Z|") for measurement (a) can be determined from the applied voltage, the voltage across a known resistor (e.g., the intrinsic strip resistance), and the voltage across the unknown impedance Vz; and similarly, for measurement (b) the phase angle can be measured from a time difference between the input and output signals by those skilled in the art.

As can be seen in graphical representation of the complex impedance plane of FIG. 5, blood samples with 3 different levels of hematocrits are tested using this technique. In FIG. 5, the vertical axis represents the imaginary and the horizontal axis represents the real impedance. As can be seen, the data points (for blood samples measured at a first frequency) with 30% hematocrit are denoted in solid circle 502, with 42% hematocrit in solid circle 504, and with 55% hematocrit in solid circle 506 to indicate the impedance |Z| of these samples on the complex impedance plane. From data points 502, 504, and 506, it turns out that at the first frequency, the phase angle $\Phi_0$ is generally constant while the impedance varies as a function of the hematocrit levels, shown here by |Z1|, |Z2| and |Z3|. In contrast, for blood samples at the second frequency higher than the first frequency, the impedance |Z4|, |Z5| and |Z6| of the various haematorcrit levels are generally constant while the phase angles $\Phi_1$, $\Phi_2$, and $\Phi_3$ change as a function of hematocrit levels (denoted at 508, 510 and 512 for 30%, 42% and 55% hematocrit, respectively).

Figure 5A:
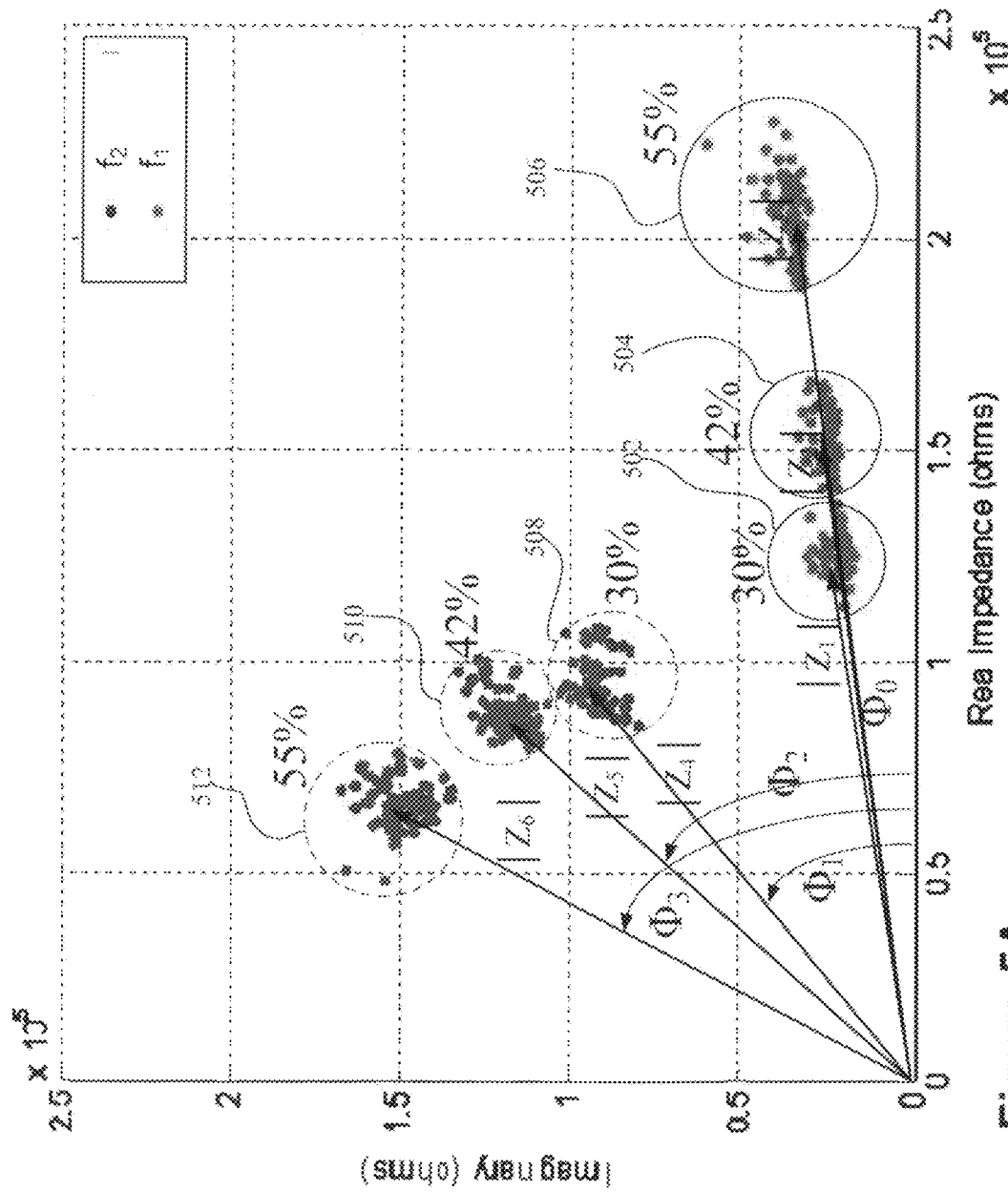
FIG. 5A illustrates a complex plane plot for glucose levels versus hematocrit levels at two frequencies.
Figure 5B:
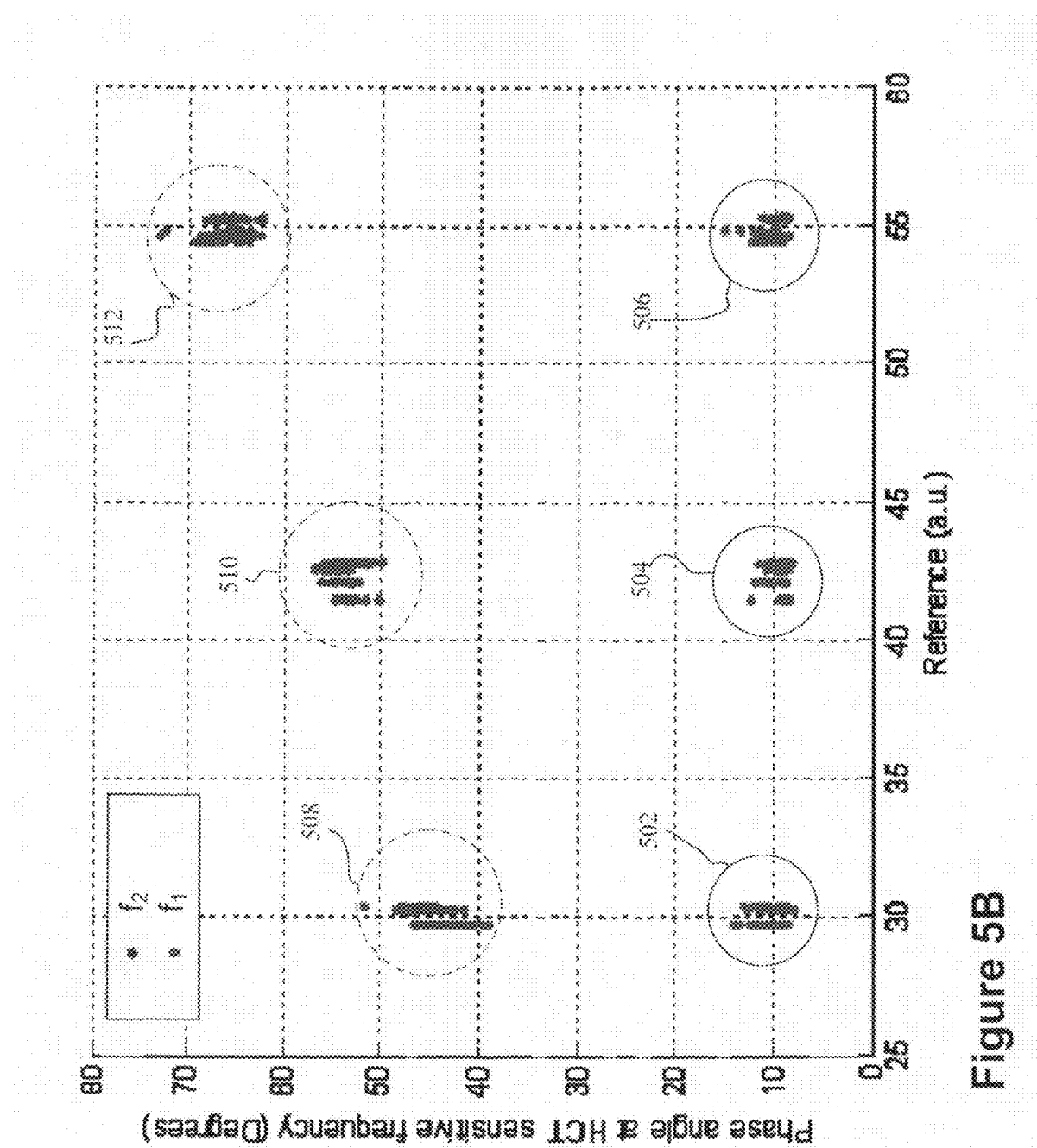
FIG. 5B illustrates a plot of the phase angle against reference hematocrit.

These interesting aspects can be seen from measurement of the phase angle with respect to the hematocrit levels in FIG. 5B. In FIG. 5B, at the first frequency (denoted by solid circles), the phase angles at about 30% hematocrit (502); at about 42% hematocrit (504); and at about 55% hematocrit (506) show generally 10 degrees for the phase angle. In contrast, as can be seen in samples measured at the higher second frequency, the phase angle at about 30% hematocrit (508) is about 45 degrees; at about 42% hematocrit (510), the phase angle is about 55 degrees; and at about 55% hematocrit (512), the phase angle is about 65 degrees. To determine the distinctions between the samples at different hematocrit levels (502, 504, and 506) at the lower first frequency, the modulus of impedance of these samples are plotted against the hematocrit level, shown here in FIG. 5C.

Figure 5C:
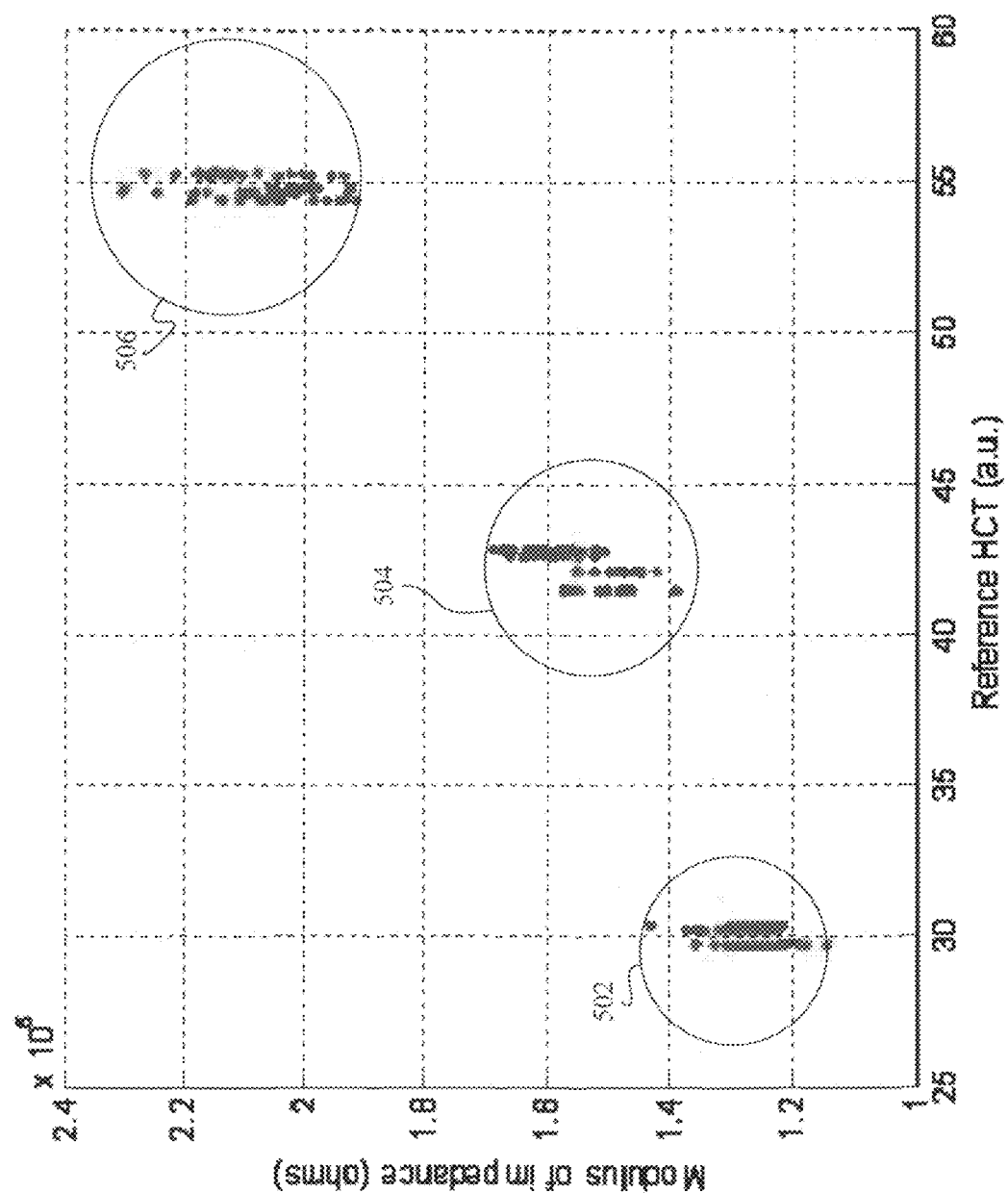
FIG. 5C illustrates a plot of the impedance against reference hematocrit.
Figure 5D:
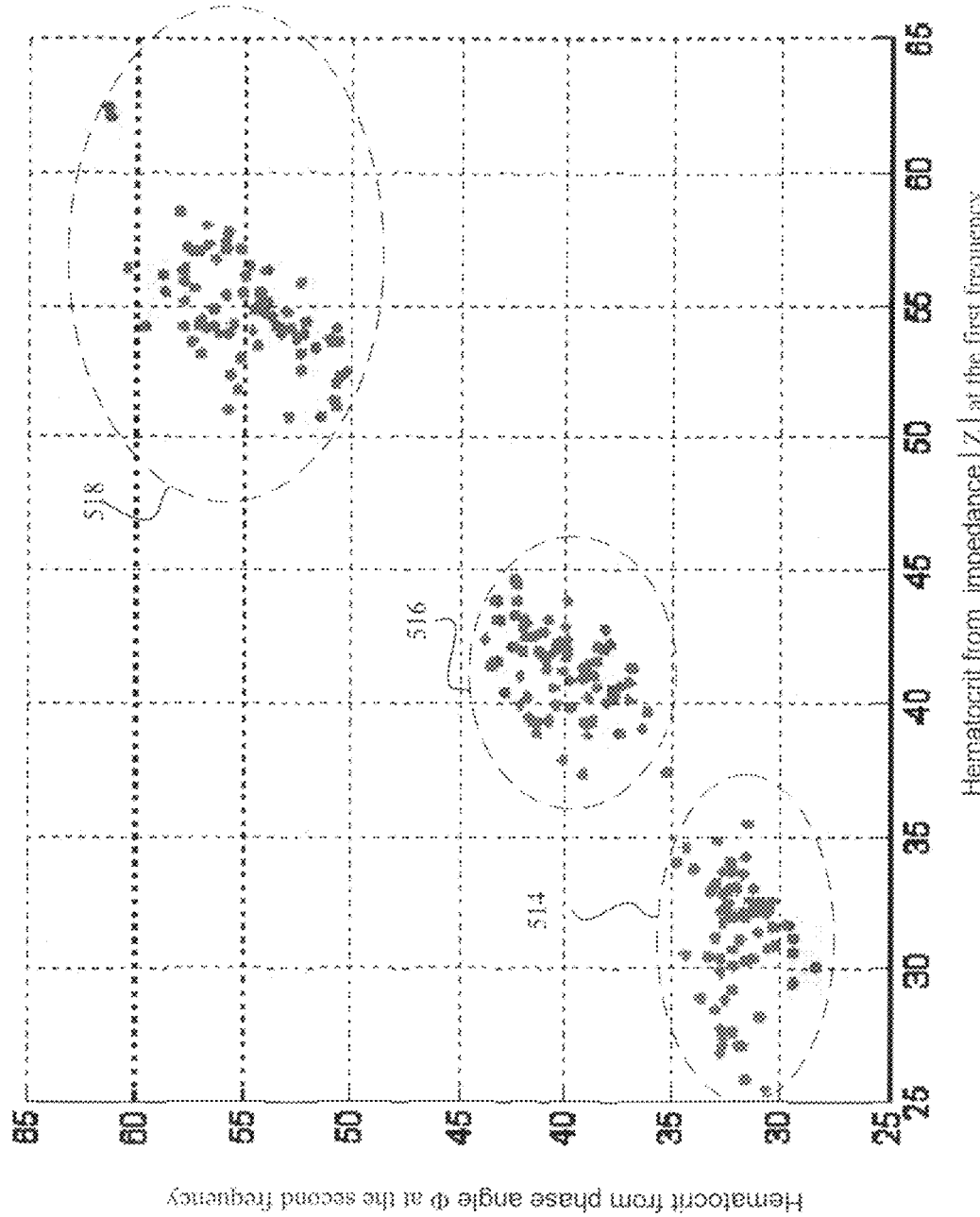
FIG. 5D illustrates a hematocrit estimates obtained by phase angle and impedance measurements.

From FIG. 5C, it can be seen that there is a clear separation in the modulus of impedance between the different levels of hematocrit (502, 504, and 506). Hence, for a first estimate of the hematocrit, applicant has utilized the distinctions in the modulus of impedance (FIG. 5C) to estimate the hematocrit. This first hematocrit estimate $HCT_{est1}$ can be represented by Equation 4:

$$HCT_{est1} = \frac{|Z| - c1}{m1}. \qquad \text{Eq. 4}$$

Where
|Z| is the measured modulus of impedance of the blood sample at one or more first frequencies lower than a second frequency;
c1 and m1 are calibration coefficients.

For a second estimate of the hematocrit, applicant has taken advantages of the distinctions in the phase angles for different levels of hematocrit at the higher second frequency (FIG. 5B) to estimate a second hematocrit level. This second hematocrit estimate $HCT_{est2}$ can be represented by Equation 5:

$$HCT_{est2} = \frac{(\Phi - c2)}{m2} \qquad \text{Eq. 5}$$

Where
$\Phi$ is the measured phase angle of the blood sample at one or more second frequencies higher than the first frequency;
c2 and m2 are calibration coefficients.

Alternatively, for increased accuracy, the second estimate of the hematocrit may be determined by using data collected for the first and second frequencies in the form of Equation 6:

$$HCT_{est2} = \frac{(\Phi_{f2} - \Phi_{f1} - c3)}{m3} \qquad \text{Eq. 6}$$

where
$\Phi_{f2}$ may be a measured phase angle of the blood sample at the second frequency f1;
$\Phi f1$ may be a measured phase angle of the blood sample at the first frequency lower than the second frequency f2;
c3 and m3 are calibration coefficients.

Figure 5E:
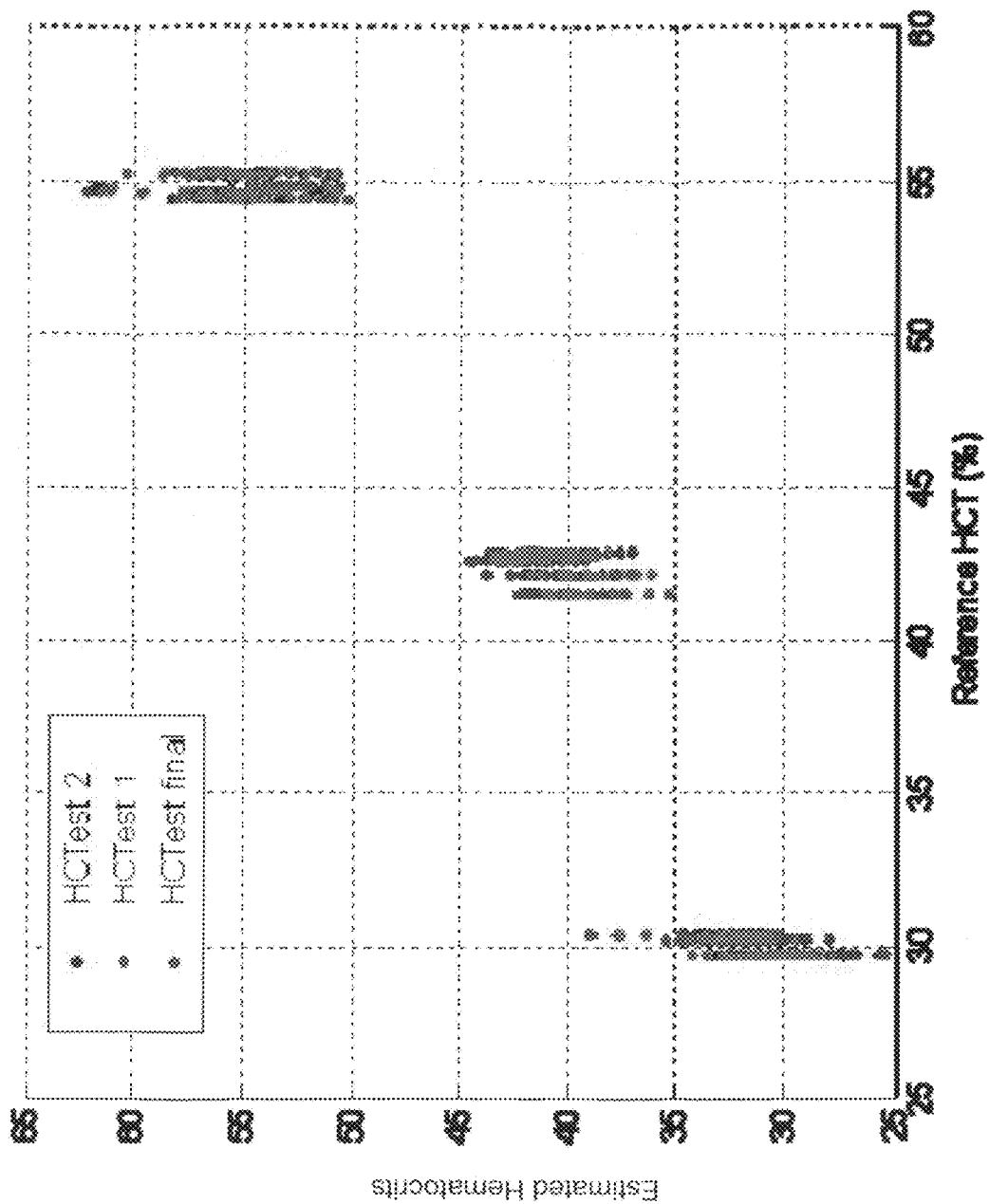
FIG. 5E illustrates a final hematocrit estimate obtained from the phase angle and impedance measurements.

From Equations 4 and 5 (or 4 and 6), applicant plotted the estimated hematocrits from both techniques against (a) phase angle at the second frequency (y-axis) and (b) impedance at the first frequency (x-axis), shown here in FIG. 5E. From FIG. 5E, the measurements show large clusterings 514, 516, and 518 of data based on both hematocrit estimation techniques, i.e., $HCT_{est1}$ from impedance Z at the first frequency and $HCT_{est2}$ from phase angle at the second frequency. To remove any outlier data, the data collected from $HCT_{est1}$ and $HCT_{est2}$ are then average out to arrive at the final hematocrit estimate $HCT_{final\_est}$ shown here in Equation 7.

$$HCT_{final\_est} = a \ast HCT_{est1} + (a-1) \ast HCT_{est2} \qquad \text{Eq. 7}$$

where $HCT_{est1}$ may be the first estimated hematocrit and $HCT_{est2}$ may be a second estimated hematocrit and $a \leq 1$ to allow for appropriate weighting of the 2 haematocrit measures, such as, for example, 60% for one estimate and 40% for the other estimate.

The final hematocrit estimate $HCT_{final\_est}$ is plotted against a referential hematocrit datum (i.e., laboratory measured hematocrit) in FIG. 5E to demonstrate the accuracy of the hematocrit estimation techniques. Thereafter, the estimated hematocrit values can be used to correct the preliminary analyte concentration $I_E$, as shown in Equation 8:

$$G_F = \frac{\left(\frac{I_E}{1 - k(HCT_{final\_est} - h_0)}\right) - c_4}{m_4}. \qquad \text{Eq. 8}$$

Where
$I_E$ represents a preliminary analyte concentration
$HCT_{final\_est}$ represents the estimated hematocrit,
$h_0$ represents nominal hematocrit,
and k, $m_4$ and $c_4$ represent parameters from regressions data.

It is noted that in the preferred embodiments, the measure of a current output for the preliminary analyte concentration is performed prior to the estimation of the hematocrit. Additional details of the technique to correct a glucose estimation with hematocrit correction is provided in International Published Application WO 2008/040998 published on Apr. 10, 2008 entitled "Systems and Methods for Determining a Substantially Hematocrit Independent Analyte Concentration," which application is incorporated by reference and attached hereto the Appendix.

By virtue of the techniques described above, a method of determining a more accurate analyte concentration can be achieved by: depositing a blood sample in a test chamber of a test strip having at least first and second electrodes in contact with a reagent and third and fourth electrodes not in contact with the reagent; driving a non-oscillating signal to the at least first and second electrodes to cause a reaction with the glucose in the blood sample and the reagent; measuring a current output of the reaction to establish a preliminary analyte concentration; applying a first oscillating input signal at a first frequency to third and fourth electrodes; determining a first estimated hematocrit based on a impedance from output signals of the third and fourth electrodes; applying a second oscillating input signal at a second frequency higher than the first frequency to the third and fourth electrodes; ascertaining a second estimated hematocrit based on a phase angle of output signals from the third and fourth electrodes; estimating a hematocrit of the blood sample based on the first and second estimated hematocrits; and deriving a final analyte concentration based on the preliminary analyte concentration and the hematocrit from the estimating step. In a variation of this method, the second frequency may be one order of magnitude higher than the first frequency; alternatively, the first frequency may be any frequency in a range of about 20,000 Hertz to about 60,000 Hertz and the second frequency comprises any frequency in a range from about 100,000 Hertz to about 1 Mega Hertz. In a further variation, a first frequency may be about 25,000 Hertz and the second frequency may be about 250,000 Hertz.

While the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:

1. A method to determine analyte concentration in a blood sample, the method comprising:
    depositing a blood sample in a test chamber of a test strip having at least first and second electrodes in contact with a reagent and third and fourth electrodes not in contact with the reagent;
    driving a non-oscillating signal to the at least first and second electrodes to cause a reaction with the glucose in the blood sample and the reagent;
    measuring a current output of the reaction to establish a preliminary analyte concentration;
    applying a first oscillating input signal at a first frequency to third and fourth electrodes, the first frequency comprising any frequency in a range of about 20,000 Hertz to about 60,000 Hertz;
    determining a first estimated hematocrit based on an impedance from output signals of the third and fourth electrodes;
    applying a second oscillating input signal at a second frequency higher than the first frequency to the third and fourth electrodes, the second frequency comprising any frequency in a range from about 100,000 Hertz to about 1,000,000 Hertz;
    ascertaining a second estimated hematocrit based on a phase angle of output signals from the third and fourth electrodes;
    estimating a hematocrit of the blood sample based on the first and second estimated hematocrits; and
    deriving a final analyte concentration based on the preliminary analyte concentration and the hematocrit from the estimating step.

2. The method of claim 1, in which the second frequency is one order of magnitude higher than the first frequency.

3. The method of claim 2, in which the first frequency comprises about 25,000 Hertz and the second frequency comprises about 250,000 Hertz.

4. The method of claim 1, in which the determining comprises utilizing an equation to determine the first estimated hematocrit $HCT_{est1}$:

$$HCT_{est1} = \frac{|Z| - c1}{m1}$$

where $|Z|$ comprises the measured modulus of impedance of the blood sample at the first frequency, $c1$ and $m1$ are calibration coefficients.

5. The method of claim 4, in which the measuring of a current output for the preliminary analyte concentration is performed prior to the estimating of the hematocrit.

6. The method of claim 4, in which the deriving comprises calculating the final analyte concentration $G_F$ from:

$$G_F = \frac{\left(\frac{I_E}{1 - k(HCT_{final\_est} - h_0)}\right) - c_4}{m_4}.$$

Where
    $I_E$ comprises a magnitude of the measured end current
    $HCT_{final\_est}$ comprises the hematocrit,
    $h_0$ comprises nominal hematocrit,
    and k, m4 and $c_4$ comprise parameters from regressions data.

7. The method of claim 1, in which the ascertaining comprises utilizing an equation to determine the second estimated hematocrit $HCT_{est2}$ of the form:

$$HCT_{est2} = \frac{(\Phi - c2)}{m2}$$

where $\Phi$ comprises a measured phase angle of the blood sample at one or more second frequencies higher than the first frequency; c2 and m2 comprise respective calibration coefficients.

8. The method of claim 1, in which the ascertaining comprises utilizing an equation to determine the second estimated hematocrit $HCT_{est2}$ of the form:

$$HCT_{est2} = \frac{(\Phi_{f2} - \Phi_{f1} - c3)}{m3}$$

where $\Phi_{f2}$ comprises a measured phase angle of the blood sample at the second frequency; $\Phi_{f1}$ comprises a measured phase angle of the blood sample at the first frequency lower than the second frequency; c3 and m3 each comprises a calibration coefficient.

9. The method of claim 1, in which the estimating comprises utilizing an equation for a final estimated hematocrit $HCT_{final\_est}$ of the form:

$$HCT_{final\_est} = a^* HCT_{est1} + (a-1)^* HCT_{est2}$$

where $HCT_{est1}$ comprises the first estimated hematocrit and $HCT_{est2}$ comprises a second estimated hematocrit and $a \leq 1$.

10. The method of claim 1, in which the analyte comprises glucose.

* * * * *